United States Patent
Horiguchi et al.

(10) Patent No.: US 10,017,751 B2
(45) Date of Patent: Jul. 10, 2018

(54) HEAT-RESISTANT ISOAMYLASE

(71) Applicant: GODO SHUSEI CO., LTD., Chuo-ku (JP)

(72) Inventors: Hirofumi Horiguchi, Matsudo (JP); Ai Iyotani, Matsudo (JP); Kazuma Shiota, Matsudo (JP)

(73) Assignee: GODO SHUSEI CO., LTD., Chuo-ku (JP)

(*) Notice: Subject to any disclaimer, the term of this patent is extended or adjusted under 35 U.S.C. 154(b) by 0 days.

(21) Appl. No.: 15/532,566

(22) PCT Filed: Dec. 4, 2015

(86) PCT No.: PCT/JP2015/084118
§ 371 (c)(1),
(2) Date: Jun. 2, 2017

(87) PCT Pub. No.: WO2016/088870
PCT Pub. Date: Jun. 9, 2016

(65) Prior Publication Data
US 2017/0362581 A1  Dec. 21, 2017

(30) Foreign Application Priority Data
Dec. 5, 2014  (JP) .................. 2014-246530

(51) Int. Cl.
*C12P 19/22* (2006.01)
*C12N 9/26* (2006.01)
(Continued)

(52) U.S. Cl.
CPC ............ *C12N 9/2411* (2013.01); *C12N 15/70* (2013.01); *C12N 15/746* (2013.01); *C12N 15/81* (2013.01);
(Continued)

(58) Field of Classification Search
None
See application file for complete search history.

(56) References Cited

U.S. PATENT DOCUMENTS

| | | |
|---|---|---|
| 2003/0190738 A1 | 10/2003 | Bisgard-Frantzen et al. |
| 2009/0280553 A1 | 11/2009 | Mikami et al. |

FOREIGN PATENT DOCUMENTS

| | | |
|---|---|---|
| CN | 102559568 | 7/2012 |
| JP | 8-23981 A | 1/1996 |

(Continued)

OTHER PUBLICATIONS

NCBI Reference Sequence WP_057156171.1, published Nov. 9, 2015.*

(Continued)

*Primary Examiner* — Richard C Ekstrom
(74) *Attorney, Agent, or Firm* — Oblon, McClelland, Maier & Neustadt, L.L.P.

(57) ABSTRACT

An isoamylase having improved heat resistance and an industrial method for producing maltose from starch.
The isoamylase is an isoamylase consisting of the amino acid sequence represented by SEQ ID NO: 1 or an isoamylase resulting from deletion, substitution, or insertion of one to several amino acid residues in the amino acid sequence represented by SEQ ID NO: 1, wherein at least valine at amino acid number 515 and methionine at amino acid number 570 are mutated to other amino acids.

9 Claims, 2 Drawing Sheets

(51) Int. Cl.
*C12N 15/70* (2006.01)
*C12N 15/74* (2006.01)
*C12N 15/81* (2006.01)
*C12P 19/16* (2006.01)
*C13K 7/00* (2006.01)

(52) U.S. Cl.
CPC ....... *C12P 19/22* (2013.01); *C12Y 302/01068* (2013.01); *C12P 19/16* (2013.01); *C13K 7/00* (2013.01)

(56) References Cited

FOREIGN PATENT DOCUMENTS

| JP | 2002-519054 A | 7/2002 | |
|---|---|---|---|
| WO | WO 00/01796 A2 | 1/2000 | |
| WO | WO 2008/015861 A1 | 2/2008 | |
| WO | WO-2014081622 A1 * | 5/2014 | ........... C12N 9/2411 |

OTHER PUBLICATIONS

Geneseq Accession No. AAR92693, published Jun. 3, 1996.*
International Search Report dated Feb. 23, 2016 in PCT/JP2015/084118 filed Dec. 4, 2015.
J. Lou, et al., Accession No. LELH02000030, Definition: *Massilia* sp. WF1 contig30, whole genome shotgun sequence. Protein ID =KLU35061.1, Database DDBJ [online], Aug. 10, 2015, 3 Pages.
S. Hizukuri, et al., "Properties of *Flavobacterium odoratum* KU Isoamylase" Starch/Stärke, vol. 48, 1996, pp. 295-300.
Kosei Takahashi, et al., "Production and application of an isoamylase from *Flavobacterium odoratum*" Enzyme and Microbial Technology, vol. 19, 1996, pp. 456-461.
Jun-ichi Abe, et al., "Expression of the Isoamylase Gene of *Flavobacterium odoratum* KU in *Escherichia coli* and Identification of Essential Residues of the Enzyme by Site-Directed Mutagenesis" Applied and Environmental Microbiology, vol. 65, No. 9, Sep. 1999, pp. 4163-4170.
Extended European Search Report (EESR) dated May 28, 2018 for European Patent Application No. 15864800.6 (8 pages).
Li, et al., "Constitutive expression of a novel isoamylase from Bacillus lentus in Pichia pastoris for starch processing", Process Biochemistry, vol. 48, No. 9, Jul. 9, 2013, pp. 1303-1310.
Database Geneseq[Online] Jul. 17, 1998, "Mature Flavobacterium isoamylase.", XP002780743, retrieved from EBI Accesion No. GSP:AAW53886, Database Accession No. AAW53886 (1 page).
Database UniProt[Online] Feb. 22, 2012, "SubName: Full=Isomylase{ECO:0000313 EMBL:AEU37049.1}; EC=3.2.1.68{ECO:0000313 EMBL:AEU37049.1};", XP002780744, retrieved from EBI Accession No. UNIPROT:G8P1Z7, Database Accession No. G8P1Z7 (2 pages).
Database Geneseq[Online] Oct. 17, 2003, "Flavobacterium odoratum isoamylase.", XP002780745, retrieved from EBI Accesion No. GSP:AAW35390, Database Accession No. AAW35390 (1 page).

* cited by examiner

[Figure 1]
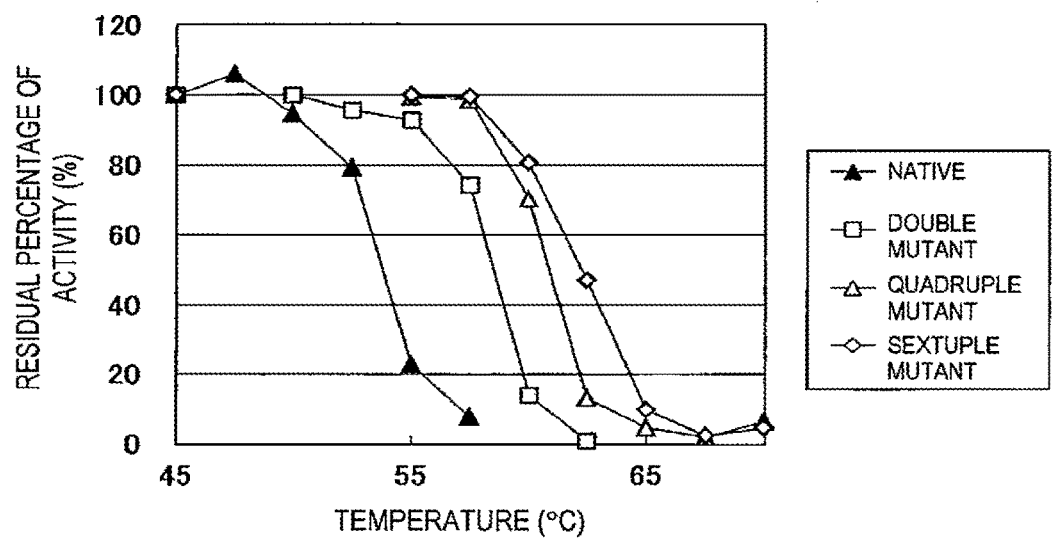
[Figure 2]
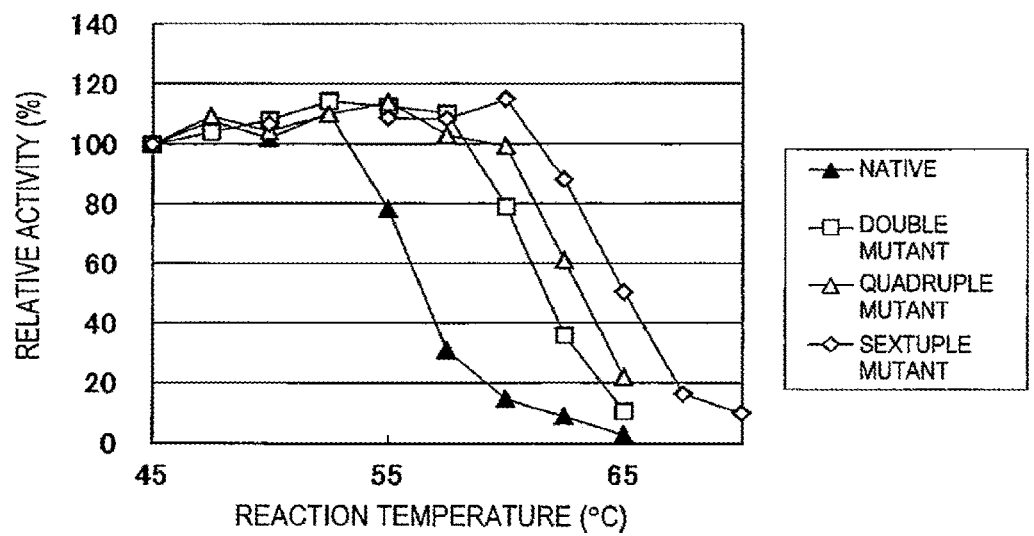

[Figure 3]
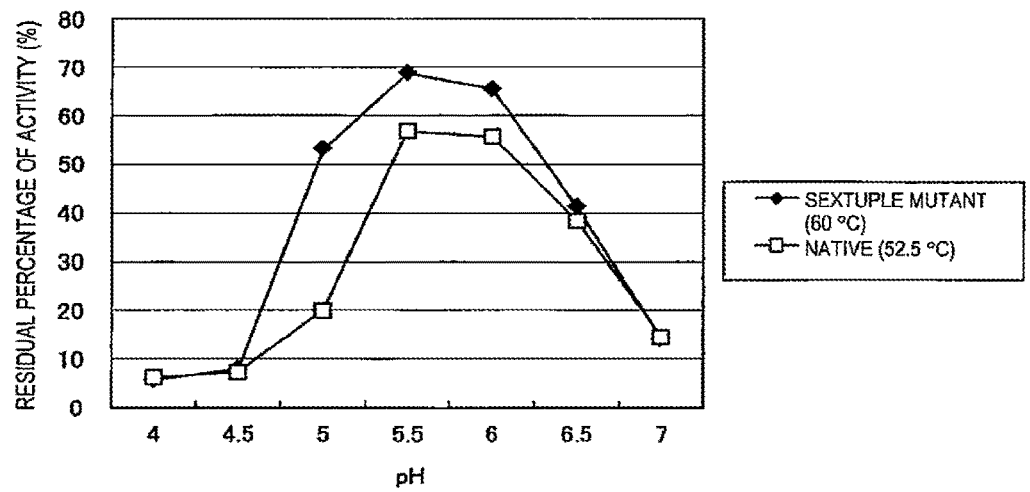
[Figure 4]
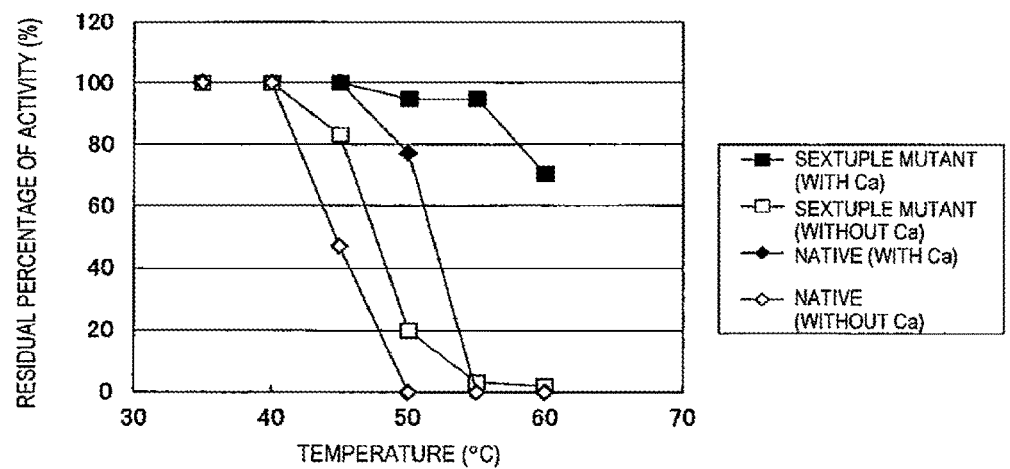

SEQUENCE LISTING

```
<160> NUMBER OF SEQ ID NOS: 3

<210> SEQ ID NO 1
<211> LENGTH: 741
<212> TYPE: PRT
<213> ORGANISM: Naxibacter haematophilus

<400> SEQUENCE: 1

Ala Ile Asn Pro Asn Lys Leu Gly Ala Ala Tyr Asp Ala Thr Lys Ala
1               5                   10                  15

Asn Val Thr Phe Lys Val Tyr Ser Ser Lys Ala Thr Arg Ile Glu Leu
            20                  25                  30

Tyr Leu Tyr Ser Thr Ala Thr Gly Ser Ala Glu Lys Ala Lys Tyr Val
        35                  40                  45

Met Thr Asn Ser Gly Gly Ile Trp Ser Val Thr Ile Pro Thr Ser Thr
    50                  55                  60

Leu Ser Gly Gln Gly Leu Gly Gly Thr Leu Tyr Tyr Gly Tyr Arg Ala
65                  70                  75                  80

Trp Gly Pro Asn Trp Pro Tyr Asn Ala Ser Trp Thr Lys Gly Ser Ser
                85                  90                  95

Leu Gly Phe Ile Ser Asp Val Asp Ala Ala Gly Asn Arg Phe Asn Pro
            100                 105                 110

Asn Lys Leu Leu Ser Asp Pro Tyr Ala Leu Glu Leu Ser His Asp Pro
        115                 120                 125

Thr Thr Ala Thr Met Thr Asn Gly Ser Ile Tyr Ala Ser Gly Ala Thr
    130                 135                 140
```

```
Tyr Arg Asn Ile Asp Ser Gly Ser Ser Ala Pro Lys Gly Ile Val Leu
145                 150                 155                 160

Ala Gly Asp Thr Gln Ala Thr Gly Thr Lys Pro Thr Arg Ala Leu Lys
            165                 170                 175

Asp Asp Val Val Tyr Glu Ala His Val Arg Gly Leu Thr Met Asn Asp
                180                 185                 190

Thr Ser Ile Thr Ala Ala Tyr Arg Gly Thr Tyr Lys Gly Ala Gly Leu
            195                 200                 205

Lys Ala Ala Ala Leu Ala Ala Leu Gly Val Thr Ala Ile Glu Phe Leu
210                 215                 220

Pro Val Gln Glu Thr Gln Asn Asp Thr Asn Asp Asn Asp Pro Ser Ser
225                 230                 235                 240

Thr Ser Gly Asp Asn Tyr Trp Gly Tyr Met Thr Leu Asn Tyr Phe Ala
            245                 250                 255

Pro Asp Arg Arg Tyr Ala Tyr Asp Lys Thr Pro Gly Gly Pro Thr Arg
                260                 265                 270

Glu Phe Lys Glu Met Val Lys Ala Phe His Asp Asn Gly Ile Lys Val
            275                 280                 285

Leu Val Asp Val Val Tyr Asn His Thr Gly Glu Gly Gly Ala Trp Ser
290                 295                 300

Pro Thr Asp Lys Thr Thr Tyr Asn Ile Thr Ser Phe Arg Gly Leu Asp
305                 310                 315                 320

Asn Pro Thr Tyr Tyr Ser Leu Thr Ala Asp Phe Gln Asn Ser Trp Asp
            325                 330                 335

Asn Thr Gly Val Gly Gly Asn Tyr Asn Thr Arg Asn Thr Ile Ala Gln
            340                 345                 350

Asn Leu Ile Val Asp Ser Leu Ala Tyr Trp Arg Asp Lys Leu Gly Val
            355                 360                 365

Asp Gly Tyr Arg Phe Asp Leu Ala Ser Val Leu Gly Asn Ser Cys Gln
        370                 375                 380

His Gly Cys Phe Asn Phe Asp Lys Met Asp Ala Gly Asn Ala Leu Asn
385                 390                 395                 400

Arg Ile Val Ala Glu Leu Pro Pro Arg Pro Ala Thr Gly Gly Ser Gly
                405                 410                 415

Val Asp Leu Ile Ala Glu Pro Trp Ala Ile Gly Gly Asn Ser Tyr Gln
            420                 425                 430

Val Gly Gly Phe Pro Ser Gly Trp Ala Glu Trp Asn Gly Ala Tyr Arg
        435                 440                 445

Asp Val Val Arg Gln Ala Gln Asn Lys Leu Gly Ser Val Ala Ile Thr
        450                 455                 460

Thr Gly Gln Met Ala Thr Arg Phe Ala Gly Ser Ser Asp Leu Tyr Gly
465                 470                 475                 480

Asp Asp Gly Arg Lys Pro Trp His Ser Val Asn Phe Ile Thr Ala His
            485                 490                 495

Asp Gly Phe Thr Leu Lys Asp Leu Tyr Ser Cys Asn Ser Lys Asn Asn
            500                 505                 510

Asn Gln Val Trp Pro Tyr Gly Pro Ser Asp Gly Glu Asp Asn Asn
        515                 520                 525

Asn Ser Trp Asp Gln Gly Ile Ala Ala Asp Gln Arg Lys Ala Ala
        530                 535                 540

Arg Asn Gly Met Ala Leu Met Met Leu Ser Ala Gly Val Pro Met Ile
545                 550                 555                 560
```

```
Val Gly Gly Asp Glu Ala Leu Arg Ser Met Asn Cys Asn Asn Asn Pro
                565                 570                 575

Tyr Asn Leu Asp Ser Ser Ala Asn Trp Leu Asn Trp Ser Arg Thr Thr
                580                 585                 590

Asp Gln Asn Asn Phe Gln Ser Phe Ser Lys Ala Met Ile Ala Phe Arg
                595                 600                 605

Lys Ala His Pro Ala Leu Arg Pro Ala Asn Phe Tyr Ser Ser Val Asp
                610                 615                 620

Asn Asn Gly Asn Val Met Glu Gln Leu Arg Trp Phe Lys Pro Asp Gly
625                 630                 635                 640

Gly Val Ala Asp Ala Thr Tyr Phe Asn Asp Ala Asn Asn His Ala Ile
                645                 650                 655

Ala Trp Arg Ile Asp Gly Ser Glu Phe Gly Asp Thr Ala Ser Ala Ile
                660                 665                 670

Tyr Val Ala His Asn Ala Trp Ser Ala Gln Val Asn Phe Thr Leu Pro
                675                 680                 685

Trp Pro Gly Ala Gly Lys Ser Trp Tyr Arg Val Thr Asp Thr Cys Gly
                690                 695                 700

Trp Ala Glu Gly Ala Ser Gln Val Gln Ala Pro Gly Ser Glu Ala Leu
705                 710                 715                 720

Val Gly Gly Glu Asn Thr Ala Tyr Gly Leu Cys Gly Arg Gly Thr Leu
                725                 730                 735

Leu Leu Ile Ala Lys
                740

<210> SEQ ID NO 2
<211> LENGTH: 27
<212> TYPE: DNA
<213> ORGANISM: Artificial Sequence
<220> FEATURE:
<223> OTHER INFORMATION: Designed primer

<400> SEQUENCE: 2
cgacgcgtgg ccaggaaccg taaaaag                                    27

<210> SEQ ID NO 3
<211> LENGTH: 29
<212> TYPE: DNA
<213> ORGANISM: Artificial Sequence
<220> FEATURE:
<223> OTHER INFORMATION: Designed primer

<400> SEQUENCE: 3
gctctagatt taagggcacc aataactgc                                  29
```

HEAT-RESISTANT ISOAMYLASE

FIELD OF THE INVENTION

The present invention relates to a mutant isoamylase having improved heat resistance and a method for producing maltose using a mutant isoamylase.

BACKGROUND ART

In the saccharification industry, pullulanase produced by *Klebsiella pneumoniae* and the like and isoamylase are known as enzymes which hydrolyze α-1,6-glucopyranoside linkages in starch and amylopectin. Of these, pullulanase catalyzes reversible reactions such as the formation of tetrasaccharides through polymerization of maltose and the transfer of maltose to amylose in the presence of a high concentration of substrates (i.e., 20% (w/v) or more). Therefore, high purity maltose is not predicable when β-amylase is used together in the production of maltose.

Meanwhile, isoamylase is an enzyme which hydrolyzes α-1,6-glucopyranoside linkages in starch, amylopectin, and glycogen, and is known to be capable of producing high purity maltose since it does not catalyze reversible reactions. As isoamylase-producing bacteria, *Pseudomonas amyloderamosa*, *Flavobacterium odoratum* (currently called *Naxibacter haematophilus*), and the like have been reported. However, isoamylases produced by these bacteria are incompatible with various amylases to be used together in terms of the optimum pH and temperature, and the like, and therefore, their capacity could not be fully demonstrated. Generally, the production of starch sugar is carried out at a high temperature of 50° C. or more and under weakly acidic conditions of pH 5.0 to 6.0, which are favorable conditions for other amylases. However, since the optimum pH of isoamylase produced by *Pseudomonas amyloderamosa* is from 3.0 to 4.0, which is shifted in the acidic region (Non Patent Literature 1), it has been difficult to use this enzyme in combination with malt β-amylase and bacterial β- and α-amylases, which have poor acid resistance. While isoamylase produced by *Flavobacterium odoratum* (currently called *Naxibacter haematophilus*) and the like is compatible with various amylases to be used together in terms of the optimum pH, its optimum temperature is as low as 40 to 45° C. (Non Patent Literatures 2 and 3). Therefore, it has been difficult to use this enzyme in combination with various amylases.

CITATION LIST

Non Patent Literature

[Non Patent Literature 1] Starch (1996), 48: 295-300
[Non Patent Literature 2] Enzyme and Microbial Technology (1996), 19(6), 456-461
[Non Patent Literature 3] Applied and Environmental Microbiology (1999), 65(9), 4163-4170

SUMMARY OF INVENTION

Technical Problem

For the industrial production of high purity maltose from polysaccharides such as starch, the combination use of amylase such as β-amylase and isoamylase is desired. However, because the optimum temperature of isoamylase produced by *Flavobacterium odoratum* and the like is lower than that of other amylases, they were not suitable for being used together.

In light of the above, an object of the present invention is to provide a novel isoamylase having further improved optimum temperature, i.e., improved heat resistance, and a method for producing maltose using this isoamylase.

Solution to Problem

In view of the foregoing, the present inventors produced proteins by partially modifying the amino acid sequence of the aforementioned isoamylase produced by *Flavobacterium odoratum* and the like and studied their heat resistance. As a result, they have found that mutant isoamylases improved in heat resistance by 5° C. to 10° C. can be obtained by mutating amino acids at two or more specific positions to other amino acids, thereby completing the present invention.

That is, the present invention provides the following [1] to [9].

[1] An isoamylase consisting of an amino acid sequence represented by SEQ ID NO: 1 or an isoamylase resulting from deletion, substitution, or insertion of one to several amino acid residues in an amino acid sequence represented by SEQ ID NO: 1, in which at least valine at amino acid number 515 and methionine at amino acid number 570 are mutated to other amino acids.
[2] The isoamylase according to [1], in which the amino acid mutations are V515P and M570L.
[3] The isoamylase according to [1] or [2], in which, further, one or more amino acid residues selected from the group consisting of serine at amino acid number 239, threonine at amino acid number 241, glycine at amino acid number 534, and serine at amino acid number 601 are mutated to other amino acids.
[4] The isoamylase according to [3], in which the amino acid mutation is one or more selected from the group consisting of S239N, T241A, G534D, and S601T.
[5] A gene encoding the isoamylase according to any one of [1] to [4].
[6] A recombinant vector comprising the gene according to [5].
[7] A transformant transformed with the recombinant vector according to [6].
[8] A method for producing an isoamylase, comprising culturing the transformant according to [7] and collecting an isoamylase from a culture thus obtained.
[9] A method for producing maltose, comprising allowing an enzyme selected from the group consisting of β-amylase and α-amylase and the isoamylase according to any one of [1] to [4] to act on starch.

Advantageous Effects of Invention

The isoamylase of the present invention is improved in heat resistance by 5° C. or more, and thus, its optimum temperature overlaps with that of various other amylases. Therefore, the industrial production of high purity maltose can be advantageously carried out by allowing the isoamylase of the present invention to act on starch and the like in combination with various amylases.

BRIEF DESCRIPTION OF DRAWINGS

FIG. 1 is a graph illustrating the heat stability of the native enzyme and each mutant enzyme.

FIG. 2 is a graph illustrating the optimum temperature of the native enzyme and each mutant enzyme.

FIG. 3 is a graph illustrating the pH stability of the native enzyme and a sextuple mutant enzyme.

FIG. 4 is a graph illustrating the improved heat resistance of the native enzyme and a sextuple mutant enzyme in the presence of calcium.

DESCRIPTION OF EMBODIMENTS

The isoamylase of the present invention is an isoamylase having the amino acid sequence represented by SEQ ID NO: 1 or an isoamylase resulting from deletion, substitution, or insertion of one to several amino acid residues in the amino acid sequence represented by SEQ ID NO: 1, wherein at least valine at amino acid number 515 and methionine at amino acid number 570 are mutated to other amino acids.

Here, the isoamylase having the amino acid sequence represented by SEQ ID NO: 1 is isoamylase produced by *Flavobacterium odoratum* (now *Naxibacter haematophilus*), which is described in Non Patent Literatures 2 and 3. The above isoamylase comprises isoamylase not derived from *Flavobacterium odoratum* as long as it has the same amino acid sequence. Further, the above isoamylase comprises not only polypeptides, but also glycopeptides as long as they have the same amino acid sequence. It should be noted that SEQ ID NO: 1 represents the amino acid sequence of a mature protein.

In the isoamylase resulting from deletion, substitution, or insertion of one to several amino acid residues in the amino acid sequence represented by SEQ ID NO: 1, the number of amino acid residues which have been deleted, substituted, or inserted is not limited as long as the resulting isoamylase exhibits an equivalent enzymatic activity to isoamylase having the amino acid sequence represented by SEQ ID NO: 1. However, the number of amino acid residues is preferably from 1 to 20, more preferably from 1 to 10, and further more preferably from 1 to 8. The identity between the isoamylase resulting from deletion, substitution, or insertion and the amino acid sequence of SEQ ID NO: 1 is preferably 80% or more, more preferably 85% or more, further more preferably 90% or more, and even further more preferably 95% or more. The percentage identity between sequences can be calculated by public or commercial software having an algorithm which performs a comparison using the reference sequence as a query sequence. For example, BLAST, FASTA, or GENETYX (the product of Genetyx Co Ltd.) can be used.

The isoamylase of the present invention is the aforementioned isoamylase, in which at least valine at amino acid number 515 and methionine at amino acid number 570 are mutated to other amino acids. When the isoamylase of the present invention is an isoamylase resulting from deletion, substitution, or insertion of one to several amino acid residues in the amino acid sequence of SEQ ID NO: 1, the amino acid numbers 515 and 570 may be changed. In this case, valine corresponding to valine 515 and methionine corresponding to methionine 570 are mutated to other amino acids. The same applies to amino acid numbers 239, 241, 534, and 601 to be described later, which refer to positions at which amino acids corresponding to amino acids before mutation are present.

Examples of other amino acids which substitute for amino acid number 515 include proline, isoleucine, leucine, glycine, and alanine, of which proline and isoleucine are more preferable, and proline is further more preferable. Accordingly, examples of mutations at amino acid number 515 include V515P, V515I, V515L, V515G, and V515A, of which V515P and V515I are more preferable, and V515P is further more preferable.

Examples of other amino acids which substitute for amino acid number 570 include leucine, isoleucine, valine, alanine, and proline, of which leucine, isoleucine, valine, and alanine are more preferable, and leucine is further more preferable. Accordingly, examples of mutations at amino acid number 570 include M570L, M570I, M570V, M570A, and M570P, of which M570L, M570I, M570V, and M570A are more preferable, and M570L is further more preferable.

The isoamylase of the present invention can achieve an improvement of 5% or more in heat resistance by at least two positions of amino acids, namely valine at amino acid number 515 and methionine at amino acid number 570, being mutated to other amino acids. The improvement in heat resistance is not satisfactory if only one of them is mutated.

The isoamylase of the present invention is preferably one in which, in addition to the aforementioned two positions, further one or more amino acid residues selected from the group consisting of serine at amino acid number 239, threonine at amino acid number 241, glycine at amino acid number 534, and serine at amino acid number 601 are mutated to other amino acids.

Here, examples of other amino acids to which serine at amino acid number 239 is mutated include asparagine and glutamine, of which asparagine is more preferable. Accordingly, examples of mutations at amino acid number 239 include S239N and S239Q, of which S239N is more preferable.

Examples of other amino acids to which threonine at amino acid number 241 is mutated include alanine, serine, and glycine, of which alanine is more preferable. Accordingly, examples of mutations at amino acid number 241 include T241A, T241S, and T241G, of which T241A is more preferable.

Examples of other amino acids to which glycine at amino acid number 534 is mutated include aspartic acid, glutamic acid, asparagine, and glutamine, of which aspartic acid and glutamic acid are more preferable, and aspartic acid is further more preferable. Accordingly, examples of mutations at amino acid number 534 include G534D, G534E, G534N, and G534Q, of which G534D and G534E are more preferable, and G534D is further more preferable.

Examples of other amino acids to which serine at amino acid number 601 is mutated include threonine, alanine, glycine, asparagine, and valine, of which threonine, alanine, and glycine are more preferable, and threonine is further more preferable. Accordingly, examples of mutations at amino acid number 601 include S601T, S601A, S601G, S601N, and S610V, of which S601T, S601A, and S601G are more preferable, and S601T is further more preferable.

While one or more of amino acid numbers 239, 241, 534, and 601 are mutated, in addition to the aforementioned 515 and 570, it is preferable that 241; 241 and 601; 239, 241, and 601; or 239, 241, 534, and 601 are mutated in consideration of the improvement in heat resistance.

Examples of more preferable multiple mutations include V515P/M570L, T241A/V515P/M570L, T241A/V515P/M570L/S601T, S239N/T241A/V515P/M570L/S601T, and S239N/T241A/V515P/G534D/M570L/S601T.

The mutant isoamylase of the present invention can be produced by using a gene which is constructed based on an isoamylase having the amino acid sequence represented by SEQ ID NO: 1 or an isoamylase resulting from deletion, substitution; or insertion of one to several amino acid residues in the amino acid sequence represented by SEQ ID NO: 1, wherein valine at amino acid number 515 and methionine at amino acid number 570 are substituted by other amino acids, and further, if necessary, one or more amino acid residues selected from the group consisting of serine at 239, threonine at 241, glycine at 534, and serine at 601 are substituted by other amino acids.

The gene for the production of the mutant isoamylase of the present invention is a gene having a base sequence encoding the aforementioned mutant isoamylase, and can be constructed by, for example, substituting the base sequence encoding the amino acid sequence to be substituted in a gene encoding the aforementioned amino acid sequence represented by SEQ ID NO: 1 by a base encoding the desired amino acid residue. Various methods of such site-specific base sequence substitution are well known in the art, and it can be performed by, for example, PCR using a properly designed primer. Alternatively, a gene encoding a modified amino acid sequence can be entirely synthesized.

The gene obtained as above is inserted into an appropriate expression vector, and a suitable host (such as *E. coli*) is transformed with the resulting vector. Numerous vector and host systems for expressing foreign proteins are known in the art. Examples of expression vectors for incorporating the gene for the mutant isoamylase include a plasmid vector, and examples of plasmid vectors for *E. coli* include pET-14b and pBR322. Examples of plasmid vectors for *Bacillus subtilis* include pUB110. Examples of plasmid vectors for filamentous fungi include pPTRI. Examples of plasmid vectors for yeasts include pRS403.

Microorganisms such as *E. coli, Bacillus subtilis*, filamentous fungi, and yeasts are transformed with the recombinant plasmid thus obtained, and the mutant isoamylase of the present invention is obtained by culturing the resulting transformant.

The isoamylase of the present invention is improved in heat resistance by 5° C. to 10° C. compared to isoamylase produced by *Flavobacterium odoratum* and the like, while having equivalent properties such as optimum pH, isoamylase activity, and calcium dependence to those of isoamylase produced by *Flavobacterium odoratum* and the like. Accordingly, high purity maltose can be easily obtained by allowing an enzyme selected from the group consisting of β-amylase and α-amylase and the isoamylase of the present invention to act on starch. Here, as β-amylase, GODO-GBA2 (Godo Shusei Co., Ltd.), OPTIMALT BBA (Danisco Japan Ltd.), β-amylase L/R (Nagase ChemteX Corporation), Himaltosin GL (HBI Enzymes•Inc.) and the like can be used. As α-amylase, for example, KLEISTASE T10 (Daiwa Fine Chemicals Co., Ltd.) can be used.

The reactions are performed by, for example, adding the above enzyme to starch and a starch saccharifying enzyme such as amylase, followed by mixing and stirring under the conditions of using the working pH and temperature of the above enzyme. The industrial production of high purity maltose can be advantageously carried out by the method of the present invention.

EXAMPLES

Next, the present invention will be described in further detail with reference to Examples; however, the present invention is not limited to these Examples in any way.

Example 1 (Site-Directed Mutagenesis on Isoamylase)

Using pHSG398 (Takara Bio Inc.) as a template and the primers MLUPHSG398-F (CGACGCGTGGCCAGGAAC-CGTAAAAAG (SEQ ID NO: 2)) and XBAPHSG398-R (GCTCTAGATTTAAGGGCACCAATAACTGC (SEQ ID NO: 3)), a fragment of about 1.5 kb was obtained. The fragment was digested with the restriction enzymes Xba I and Mlu I, followed by ligation with an Xba I-Mlu I fragment of about 2.5 kb carrying the isoamylase gene on the genome of *Flavobacterium odoratum* to obtain p-ML. Site-directed mutagenesis was performed on the plasmid p-ML, which is an expression plasmid for the native isoamylase, to obtain the expression plasmid p-W for a double mutant (V515P/M570L). Further, site-directed mutagenesis was performed on this plasmid to obtain the expression plasmid p-Q for a quadruple mutant (T241A/V515P/M570L/S601T) and the expression plasmid p-S for a sextuple mutant (S239N/T241A/V515P/G534D/M570L/S601T).

Example 2 (Production of Enzymes)

The expression plasmid p-ML for the native isoamylase, the expression plasmid p-W for the double mutant, the expression plasmid p-Q for the quadruple mutant, and the expression plasmid p-S for the sextuple mutant were used for the transformation of the *E. coli* strain DH5α to obtain *E. coli* strains producing respective isoamylases. The *E. coli* thus obtained was cultured in LB media containing 30 μg/ml chloramphenicol (0.5% yeast extract, 1.0% tryptone, 0.5% sodium chloride, pH 7.2) at 30° C. for three days to obtain 1 L of culture solutions. Bacterial cells were removed by centrifugation (10,000 g, 10 minutes), followed by UF concentration (AIP module, the product of Asahi Kasei Corporation) to 10,000 U/ml. The resulting solutions were sterilized using a membrane having a pore size of 0.2 μm, whereby enzyme solutions of the native isoamylase, double mutant isoamylase, quadruple mutant isoamylase, and sextuple mutant isoamylase were obtained.

Example 3 (Improved Heat Stability of Each Mutant)

The above enzyme solutions were kept at 45° C., 47.5° C., 50° C., 52.5° C., 55° C., 57.5° C., 60° C., 62.5° C., 65° C., 67.5° C., and 70° C. for 10 minutes, followed by rapid cooling. Then, the residual activity was measured.
<Method for Measuring the Activity>
The method for measuring the isoamylase activity is as follows.
Acetic acid buffer (0.5 M, pH 6.0, 0.1 ml) is mixed with 0.35 ml of a 0.5% waxy corn starch solution. To the resulting solution, 0.1 ml of the enzyme solution diluted at an appropriate time is added, followed by reaction at 45° C. for 15 minutes. Subsequently, the enzymatic reaction is terminated by adding 0.5 ml of an iodine solution (a 0.5 M potassium iodide solution containing 0.05 M iodine) diluted 5-fold with 0.1 N HCl, followed by the addition of 10 ml of water and thorough stirring. Then, a measurement is taken at 610 nm using a spectrophotometer. One unit of the enzymatic activity was defined as the amount of enzyme required to increase absorbance by 0.01 in one minute under the aforementioned conditions.

As a result, as shown in FIG. 1, it was confirmed that the heat resistance of the double mutant was improved by about 5° C., the quadruple mutant by about 8° C., and the sextuple mutant by about 10° C.

Example 4 (Increased Optimum Temperature)

While the optimum temperature of the native enzyme is normally 45° C., the activities of the native and respective mutant enzymes thus obtained at 47.5° C., 50° C., 52.5° C., 55° C., 57.5° C., 60° C., 62.5° C., 65° C., 67.5° C., and 70° C. were measured by the method described in Example 3.

As a result, as shown in FIG. 2, it was found that the higher the degree of multiplicity of mutation, the higher the optimum temperature (i.e., the optimum temperature was highest in the sextuple mutant, followed by the quadruple mutant, and then by the double mutant).

Example 5 (Optimum pH)

The pH stability of the native isoamylase and the sextuple mutant was examined. At each of pH 4.0, 4.5, 5.0, 5.5, 6.0, 6.5, and 7.0, the sextuple mutant was kept at 60° C. and the native isoamylase at 52.5° C. for 10 minutes, followed by rapid cooling. Then, the residual activity was measured by the method described in Example 3.

As a result, there was no major shift in the optimum pH range due to amino acid modification.

Example 6 (Calcium Dependence)

The calcium dependence associated with heat resistance was examined in the native isoamylase and the sextuple mutant. The native isoamylase and the sextuple mutant were kept warm at 35° C., 40° C., 45° C., 50° C., 55° C., and 60° C. for 10 minutes in 20 mM acetate buffer containing 10 mM calcium chloride (pH 6.0) or in 20 mM acetate buffer containing no calcium chloride (pH 6.0), followed by rapid cooling. Then, the residual activity was measured by the method described in Example 3.

As a result, as shown in FIG. 4, both the native isoamylase and the sextuple mutant exhibited high heat resistance in the presence of calcium.

Example 7 (Production of Maltose Syrup)

A test of the purification of maltose from dextrin was performed. As dextrin, Pinedex #100 (the product of Matsutani Chemical Industry Co., Ltd.) was dissolved in 10 mM acetate buffer (pH 6.0) so as to achieve Brix 30, and reactions were allowed to proceed in each of (1) a mixture obtained by adding 0.2 mg of GODO-GBA2 (the product of Godo Shusei Co., Ltd.) per g dextrin, (2) a mixture obtained by adding 0.2 mg of GODO-GBA2 per g dextrin and 400 U of the native isoamylase per g dextrin, and (3) a mixture obtained by adding 0.2 mg of GODO-GBA2 per g dextrin and 400 U of the sextuple mutant isoamylase per g dextrin at 60° C. for 24 hours.

The reactions were terminated by heating at 100° C. for five minutes, and the amount of maltose produced was measured by high-performance liquid chromatography (2695, the product of Waters Corporation) using an RI detector (2414, the product of Waters Corporation) and the CARBOSep CHO-620CA column (the product of Transgenomic, Inc.) at a column temperature of 85° C. and at a flow rate of 0.5 ml/minute, using water as an eluent.

As a result, the maltose concentration was found as (1) 15.4%, (2) 23.4%, and (3) 25.4%, showing that the greatest amount of maltose was produced when the sextuple mutant isoamylase was used.

When the test was conducted at a reaction temperature of 62° C. for more strictly preventing bacterial contamination during the reaction, the maltose concentration was found as (1) 14.0%, (2) 14.7%, and (3) 21.1%, showing that while the native isoamylase hardly exhibited the debranching effect, the sextuple mutant isoamylase exhibited the debranching effect. These results demonstrated that there was an improvement in yield.

The invention claimed is:

1. An isoamylase consisting of the amino acid sequence of SEQ ID NO: 1 or an isoamylase resulting from deletion, substitution, or insertion of one to twenty amino acid residue in the amino acid sequence of SEQ ID NO: 1,
   wherein at least valine at amino acid number 515 and methionine at amino acid number 570 are mutated to proline and leucine, respectively.

2. The isoamylase according to claim 1, wherein further at least one amino acid residue selected from the group consisting of serine at amino acid number 239, threonine at amino acid number 241, glycine at amino acid number 534, and serine at amino acid number 601 is mutated to other amino acid.

3. The isoamylase according to claim 2, wherein the amino acid mutation is at least one selected from the group consisting of S239N, T241A, G534D, and S601T.

4. A gene encoding the isoamylase according to claim 1.

5. A recombinant vector comprising the gene according to claim 4.

6. A transformant transformed with the recombinant vector according to claim 5.

7. A method for producing an isoamylase, comprising:
   culturing the transformant according to claim 6 to obtain a culture; and
   collecting an isoamylase from the culture.

8. A method for producing maltose, comprising:
   adding an enzyme selected from the group consisting of β-amylase and α-amylase and the isoamylase according to claim 1 to starch, to act on the starch.

9. An isoamylase comprising the amino acid sequence of SEQ ID NO: 1 or an isoamylase resulting from deletion, substitution, or insertion of one to twenty amino acid residue in the amino acid sequence of SEQ ID NO: 1,
wherein at least valine at amino acid number 515 and methionine at amino acid number 570 are mutated to proline and leucine, respectively.

* * * * *